United States Patent [19]  [11] 4,021,469
Weston  [45] May 3, 1977

[54] PROCESS FOR PREPARING N-PHENYLCARBAMATES

[75] Inventor: George Oliver Weston, Havant, England

[73] Assignee: John Wyeth & Brother Limited, Maidenhead, England

[22] Filed: Nov. 24, 1975

[21] Appl. No.: 634,566

[30] Foreign Application Priority Data

Dec. 3, 1974  United Kingdom ............ 52244/74

[52] U.S. Cl. .................... 260/471 C; 260/239 BD; 260/294.8 R; 260/294.8 G; 260/295 CA; 260/325 R; 260/332.2 A; 260/340.5; 260/347.2; 260/347.4; 260/470; 260/558 P; 260/570 AB

[51] Int. Cl.$^2$ ............ C07C 125/06; C07D 213/50; C07D 307/46; C07D 333/22

[58] Field of Search ........... 260/471 C, 325 R, 470, 260/340.5, 295 CA, 332.2 A, 347.4, 294.8 R, 294.8 G, 347.2

[56] References Cited

UNITED STATES PATENTS 3,428,644  2/1969  Madison et al. ............... 260/296 B
3,712,892  1/1973  Snaba et al. ................ 260/295 CA

*Primary Examiner*—Jane S. Myers

[57] ABSTRACT

Alkyl or Aralkyl N-[2-aroyl]phenylcarbamates are prepared by reacting a 3-aryl-2-indolinone with oxygen in the presence of an alkali metal alkoxide or aralkoxide.

7 Claims, No Drawings

PROCESS FOR PREPARING N-PHENYLCARBAMATES

This invention relates to a novel process for the preparation of substituted N-phenylcarbamate esters.

It has now suprisingly been found that 3-aryl-2-indolinones may be reacted with molecular oxygen in the presence of an alkali metal alkoxide or aralkoxide using the novel process of this invention to produce alkyl or aralkyl N-[2-aroyl]-phenylcarbamates.

The foregoing carbamate esters produced by the novel process are valuable chemical intermediates which are useful in the preparation of 2-aroylanilines which themselves are inter alia valuable intermediates in the preparation of therapeutically active compounds such as benzodiazepines, quinazolines and the like. For example Sternbach et al., J. Org. Chem., 27, 3788–3796 (1962) and U.K. Pat. Specifications Nos. 864,825, 948,888, 972,967, 1,211,731 and 1,341,800 disclose processes whereby 2-aroylanilines may be converted to quinazolines and benzodiazepines. Further many of the foregoing carbamate esters may be converted directly to pharmaceutically active quinazolinones by the method described in U.K. Pat. Specification No. 1,353,789 or to analogous compounds such as those disclosed in U.K. Pat. Specification 1,195,066 or to related compounds of the same general class; thereby enabling investigation of structure/activity relationships. In particular, the novel process of this invention provides a simple and convenient process for preparing 2-aminobenzophenones, in particular 2-amino-2'5-dichlorobenzophenone which is a valuable chemical intermediate as shown hereinafter.

The reaction of 3-homo or heteroaryl-oxindoles with sodium hydride or lithium, sodium or potassium hydroxide and oxygen to give homo or heteroaryl-2-aniline ketones has been previously described in U.S. Pat. No. 3,428,644. However the process disclosed in that patent does not teach or suggest that valuable stable carbamic acid esters may be obtained when the reaction is carried out in the manner disclosed herein which uses an alkali metal alkoxide or aralkoxide and oxygen.

Accordingly in one aspect, the present invention provides a novel process for preparing alkyl or aralkyl N-[2-aroyl]phenylcarbamates which comprises reacting a 3-aryl-2-indolinone with oxygen in the presence of an alkali metal alkoxide or aralkoxide.

In a preferred embodiment the present invention provides a process for preparing a 2-alkoxycarbonylaminobenzophenone having the general formula:

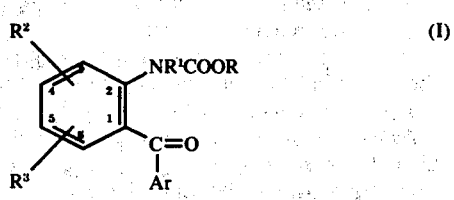

(I)

wherein R represents lower alkyl or aralkyl of 7 to 10 carbon atoms; $R^1$ represents hydrogen or a lower alkyl radical; $R^2$ and $R^3$ independently represent hydrogen, halogen, lower alkyl, lower alkoxy, nitro, lower alkylsulphonyl, lower alkylthio and trihaloalkyl; and when taken together $R^2$ and $R^3$ represent a methylenedioxy (i.e. —O—$CH_2$—O—) radical; and Ar represents an aryl radical which may be substituted or unsubstituted, which comprises reacting a compound having the general formula:

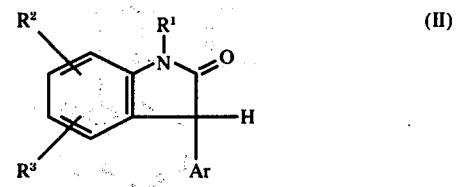

(II)

wherein $R^1$, $R^2$, $R^3$ and Ar are as hereinbefore defined, with oxygen in the presence of an alkali metal alkoxide or aralkoxide having the formula:

$$RO^-M^+ \quad \text{(III)}$$

wherein R represents lower alkyl, or aralkyl of 7 to 10 carbon atoms and $M^+$ represents an alkali metal cation.

The term "lower" as used herein in connection with the lower alkyl group means that the alkyl group has from 1 to 6 carbon atoms, preferably 1 to 4 carbon atoms. By the term aryl is meant a carbocyclic or heterocyclic radical possessing aromatic character. By the term aroyl and aralkyl is meant an arylcarbonyl or arylalkyl radical wherein aryl is as defined above. Preferred aryl radicals are carbocyclic radicals of 6 to 10 carbon atoms or monoheterocyclic radicals containing one heteroatom, such as nitrogen or sulphur, e.g. pyridyl.

Examples of the group R are methyl, ethyl, n-propyl, n-butyl and benzyl. Preferably R is methyl. Examples of $M^+$ are sodium and potassium cations, preferably $M^+$ is the sodium cation. Examples of the group $R^1$ are hydrogen, methyl, ethyl, n-propyl and n-butyl. The groups $R^2$ and $R^3$ may be exemplified by hydrogen, methyl, ethyl, n-propyl, isopropyl, chlorine, bromine, methoxy, ethoxy, nitro, methylsulphonyl, methylthio and trifluoromethyl. Examples of the group Ar when carbocyclic aryl are phenyl and phenyl substituted by halogen (for example, fluorine, chlorine or bromine), trifluoromethyl, lower alkyl, (e.g. methyl, ethyl, n-propyl, n-butyl) lower alkoxy, (e.g. methoxy ethoxy, n-propoxy), nitro and methylthio. Examples of Ar when heterocyclic aryl are pyridyl, e.g. 2-pyridyl, thienyl and furyl which may be substituted by the same groups as mentioned above for phenyl. Preferred Ar groups are phenyl, chlorophenyl, e.g. ortho- or parachlorophenyl and pyridyl. When $R^2$ is hydrogen preferred $R^3$ groups are chlorine (e.g. 5-chloro) and nitro (e.g. 5-nitro).

Accordingly a particularly preferred embodiment of the present invention provides a novel process for preparing a compound of formula

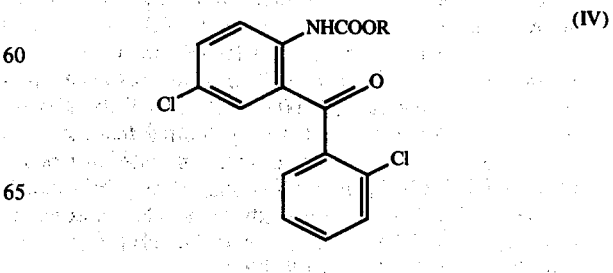

(IV)

wherein R is as defined above (preferably lower alkyl, e.g. methyl) which comprises reacting a compound of formula:

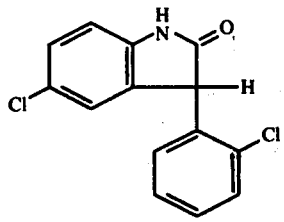

(V)

with oxygen in the presence of an alkali metal alkoxide, or aralkoxide, e.g. a lower alkoxide such as sodium methoxide, sodium ethoxide, potassium methoxide, potassium ethoxide and potassium isopropoxide.

The novel process of this invention may be carried out by passing a stream of oxygen, which may be a mixture, as in air or pure oxygen into a solution of the indolinone in an alkali metal alkoxide or aralkoxide/alkanol or aralkanol mixture. Preferably sodium methoxide/methanol is used but other mixtures such as sodium ethoxide/ethanol, potassium ethoxide/ ethanol and potassium isopropoxide/isopropanol may be used. The alcohol present in these mixtures acts as a solvent. However, other polar solvents may be used, for example dimethylformamide and the like.

Although temperature does not appear to be critical the reaction may be conveniently carried out at between about 0° and about 60° C, e.g. at about room temperature.

Without wishing to be bound to any particular scheme the following is proposed as a possible route for the novel process of this invention using the particularly preferred embodiment as an example:

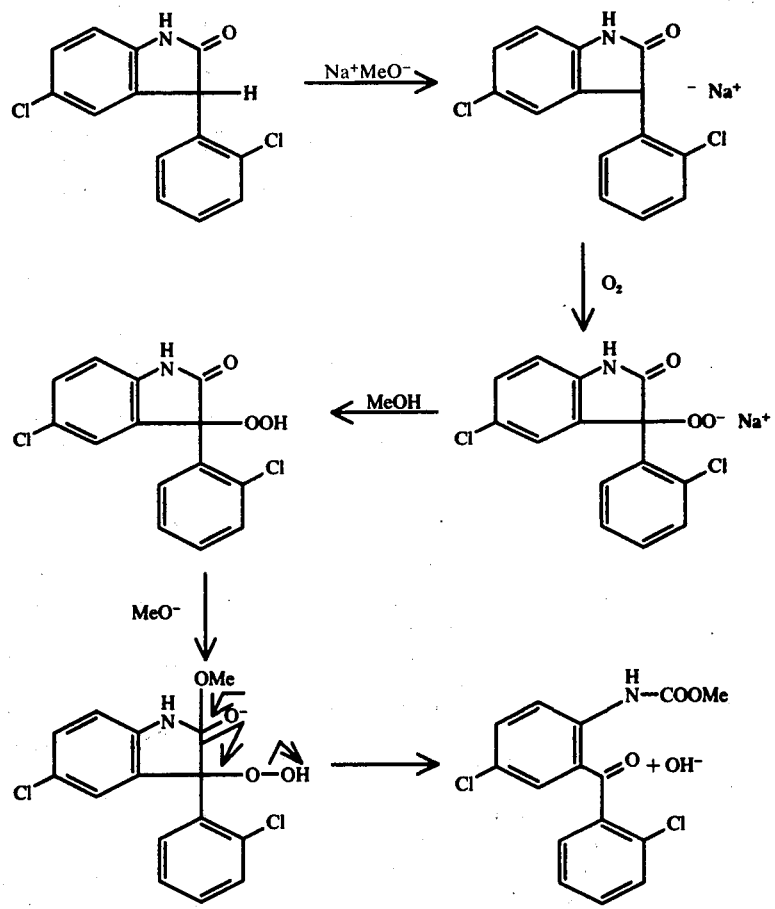

Some of the alkyl or aralkyl N-[2-aroyl]phenylcarbamates prepared by the process of this invention are novel compounds. In particular the compounds having the formula (IV) are novel compounds and are included within scope of the present invention.

As stated above the alkyl or aralkyl N-[2-aroyl]phenylcarbamates are intermediates for the preparation of 2-aroylanilines. Such a conversion may be carried out by hydrolysing the 2-alkoxy- or 2-aralkoxycarbonylaminobenzo-phenones (for example using an alkali metal hydroxide, e.g. sodium or potassium hydroxide, followed by acidification and loss of $CO_2$) to give the 2-aroylanilines. More particularly a further aspect of this invention provides a process for preparing a compound of formula:

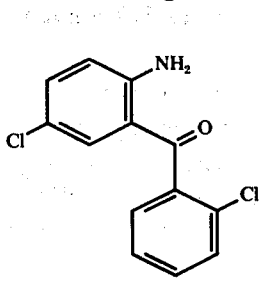
(VI)

which comprises hydrolysing a compound of formula (IV) as hereinbefore defined. If desired in the process above the compound of formula (IV) may be prepared in situ from a compound of formula (V) using the aforementioned novel process of this invention. The compound of formula (IV) may then be reacted, without isolation to give the aminobenzophenone of formula (VI).

Such a compound of formula (VI) is particularly useful for the preparation of 7-chloro-5-(o-chlorophenyl)1,3-dihydro-3-hydroxy-2H-1,4-benzodiazepin-2-one (XII).

For example, the compound of formula VI may be reacted with chloracetyl chloride to give 2-chloracetamido-2',5-dichlorobenzophenone, which compound may be reacted with sodium iodide, hydroxylamine and acid to give a compound of formula XI as shown in the following scheme:

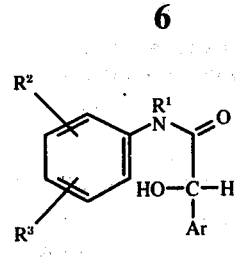
(VII)

wherein $R^1$, $R^2$, $R^3$ and Ar are as defined above in the presence of an acid such as concentrated sulphuric acid, e.g. 95–100%. The cyclisation proceeds at about 20° C. The compound of formula (VII) itself may be prepared by condensing an aniline of formula:

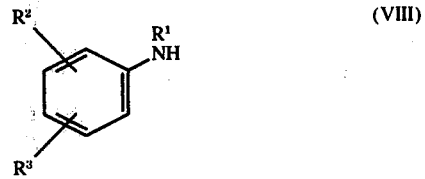
(VIII)

wherein $R^1$, $R^2$ and $R^3$ are as hereinbefore defined with a compound of formula:

$$\underset{\text{ArCHCOOH}}{\overset{\text{OH}}{|}} \quad \text{(IX)}$$

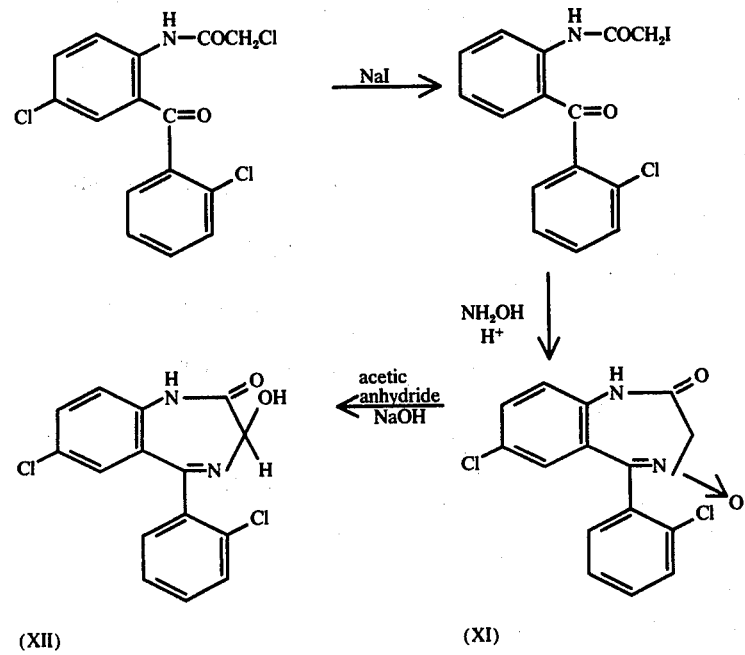

(XII)            (XI)

The conversion of XI to XII shown as the final step in the scheme above may be carried out according to the method disclosed by Bell and Childress, J. Org. Chem, 27, 1691–1695 (1962).

The 3-aryl-2-indolinones used as starting materials in the process of this invention are either known compounds or may be prepared by known procedures, for example, by procedures described in U.S. Pat. No. 2,759,935. Thus a compound of formula (II) as defined above may be prepared by cyclising a compound of formula:

wherein Ar is as hereinbefore defined, using standard procedures.

If necessary, in any of the reactions hereinbefore described reactive substituent groups may be blocked during a reaction and released at a later stage.

The following non limiting Examples illustrate the invention, where temperatures are in ° C. Examples 1, 3 and 5 to 10 illustrate the novel process of this invention and Example 2 illustrates the conversion of the product of Example 1 to a valuable chemical intermediate. Example 4 illustrates the novel process of this invention wherein the carbamate formed is converted in situ to a valuable chemical intermediate.

EXAMPLE 1

Methyl N-[4-chloro-2-o-chlorobenzoyl]-phenylcarbamate

5-Chloro-3-(o-chlorophenyl)oxindole (10 g.) was dissolved in a methanolic solution of sodium methoxide prepared by dissolving sodium (1.2 g) in methanol (100 ml.). Oxygen was blown into the solution via a sintered glass sparge tube. After one hour the precipitated product was collected, washed with methanol and dried to give the title compound as yellow crystals m.p. 116°–8°, yield 6.7 g.

Further treatment of the reaction liquors with oxygen gave an additional 1.5 g, m.p. 116°–8°, for a total yield 8.2 g. (70.3%). Recrystallisation from methanol gave the analytical sample, m.p. 116°–8°.

Analysis: Found: C 55.76, H 3,35, N 4.29%; $C_{15}H_{11}NCl_2O_3$ requires: C 55.56, H 3.42, N 4.32%.

EXAMPLE 2

2-Amino-2′,5-dichlorobenzophenone

Methyl N-[4-chloro-2-o-chlorobenzoyl]-phenylcarbamate prepared according to Example 1 was refluxed for 2 hours with a solution of potassium hydroxide (5 g.) in methanol (200 ml.). The resulting solution was cooled, acidified with hydrochloric acid and diluted with water. The product was extracted into dichloromethane and the dried extract evaporated under reduced pressure to give the title compound as a yellow powder m.p. 85°–86°, assay 94.65% (by UV, 393 mµ in methanol).

EXAMPLE 3

Methyl N-[2-benzoyl-4-chloro]-phenylcarbamate

A solution of sodium methoxide was prepared from sodium (2.4 g.) and methanol (300 ml) and 5-chloro-3-phenyloxindole (20g.) added. Oxygen was passed into the resulting solution through a sintered glass sparge tube at a temperature of 0° – 10°. After 3 hours the crystalline precipitate was collected, washed with methanol and dried to give the title compound as a yellow crystalline powder m.p. 93°–5°; yield 2.5 g. Recrystallisation from methanol gave the analytical sample as pale yellow plates m.p. 92.5°–94°. Found C 62.09, 62.03; H, 4.15; 4.10; N 4.70, 4.80%.$C_{15}H_{12}NClO_3$ requires C 62.10; H, 4.15; N 4.83%.

EXAMPLE 4

2-Amino-2′,5-dichlorobenzophenone

Sodium methoxide 27% solution in methanol (1.44 kg actual weight) was added to a stirred suspension of 3-o-chlorophenyl-5-chloroxindole (0.88 kg.) in methanol (7.00 kg.) and air blown through the resulting solution until chromatographic analysis of a sample showed that reaction was complete. Water (2.20 kg.) was added and the mixture was heated to reflux for 2 hours. After cooling the mixture was cautiously acidified with hydrochloric acid then again made basic by addition of sodium hydroxide solution. Water (2.64 kg.) was then added to precipitate the product which was recovered by filtration, washed with 1:1 aqueous methanol (0.80 kg.) and dried in a circulating air oven at 50°–60° to give 0.665 kg. (79% of theory) of 2-amino-2′,5-dichlorobenzophenone as a yellow powder, m.p. 88°, assay (UV)91.8%.

EXAMPLE 5

Methyl N-[2-benzoyl-4-bromo]phenylcarbamate

Using a procedure analogous to Example 1 5-bromo-3-phenyloxindole in a methanolic solution of sodium methoxide may be reacted with oxygen to give the title compound.

EXAMPLE 6

Methyl N-[4-bromo-2(2-pyridyl)]phenylcarbamate

Using a procedure analogous to Example 1 5-bromo-3-(2-pyridyl)oxindole in a methanolic solution of sodium methoxide may be reacted with oxygen to give the title compound.

EXAMPLE 7

Ethyl N-[2-benzoyl-4-trifluoromethyl]phenylcarbamate

Using an analogous procedure to Example 1 3-phenyl-5-trifluoromethyloxindole in an ethanolic solution of potassium ethoxide may be reacted with oxygen to give the title compound.

EXAMPLE 8

Ethyl N-[2-benzoyl-4-nitro]phenylcarbamate

Using an analogous procedure to Example 1 3-phenyl-4-nitrooxindole in an ethanolic solution of sodium ethoxide may be reacted with oxygen to give the title compound.

EXAMPLE 10

Isopropyl N-[4-chloro-2-o-chlorobenzoyl]phenylcarbamate

Using an analogous procedure to Example 1 5-chloro-3-(o-chlorophenyl)oxindole in an isopropanolic solution of potassium isopropoxide may be reacted with oxygen to give the title compound.

I claim:

1. A process for preparing a compound of general formula:

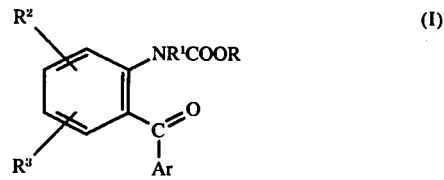

(I)

wherein R represents lower alkyl or aralkyl of 7 to 10 carbon atoms; $R^1$ represents hydrogen or a lower alkyl group; $R^2$ and $R^3$ independently represent hydrogen, halogen, lower alkyl, lower alkoxy, nitro, lower alkylsulphonyl, lower alkylthio or trifluoromethyl; and when taken together $R^2$ and $R^3$ represent methylenedioxy; and Ar represents a carbocyclic aryl radical of 6 to 10 carbon atoms, or a pyridyl, thienyl, or furyl radical, which radicals may be substituted by halogen, trifluoromethyl, lower alkyl, lower alkoxy, nitro, or methylthio; which comprises reacting in a polar solvent a compound having the general formula:

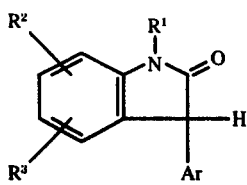

wherein $R^1$, $R^2$, $R^3$ and Ar are as hereinbefore defined, with oxygen in the presence of an alkali metal alkoxide or aralkoxide having the formula:

$$RO^- M^+ \quad (III)$$

wherein R represents lower alkyl, or aralkyl of 7 to 10 carbon atoms and $M^+$ represents an alkali metal cation.

2. A process as claimed in claim 1 wherein R represents a lower alkyl radical or aralkyl radical of 7 to 10 carbon atoms; $R^1$ represents hydrogen or a lower alkyl radical; $R^2$ and $R^3$ independently represent hydrogen, halogen, nitro and trifluoromethyl, Ar represents a phenyl radical optionally substituted by halogen or a pyridyl radical, and $M^+$ represents a sodium or potassium ion.

3. A process as claimed in claim 2 wherein R represents lower alkyl, $R^2$ represents hydrogen, $R^3$ represents chlorine and Ar represents o-chlorophenyl.

4. A process as claimed in claim 1 which is carried out in the temperature range from about 0 to about 60° C.

5. A process as claimed in claim 1 wherein R represents methyl, $M^+$ represents the sodium ion and the reaction is carried out in methanol solvent.

6. A process as claimed in claim 1 for preparing a compound of formula

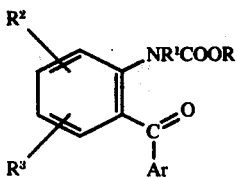

wherein R, $R^1$, $R^2$, $R^3$ and Ar are as defined in claim 1, which comprises reacting an aniline of formula

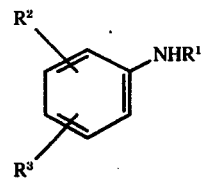

with an acid of formula $$\underset{\text{ArCHCOOH}}{\overset{OH}{|}} \quad (IX)$$

to give a compound of formula (VII)

in which formulae $R^1$, $R^2$, $R^3$ and Ar are as herein defined; cyclising the compound of formula (VII) in the presence of an acid to give a compound of formula:

(II)

wherein $R^1$, $R^2$ and $R^3$ and Ar are as herein defined; and reacting the compound of formula (II) with oxygen in the presence of an alkali metal alkoxide or aralkoxide of formula $$RO^- M^+ \quad (II)$$

wherein $M^+$ represents an alkali metal cation and R is as herein defined.

7. A process as claimed in claim 6 wherein R represents lower alkyl, $R^1$ and $R^2$ represent hydrogen, $R^3$ represents chlorine positioned para to the nitrogen, Ar represents o-chlorophenyl and $M^+$ represents the potassium or sodium cation.

* * * * *